United States Patent
Lachmanovich et al.

(10) Patent No.: US 11,382,573 B2
(45) Date of Patent: Jul. 12, 2022

(54) SYSTEM AND METHOD OF PROVIDING DISTANCE AND ORIENTATION FEEDBACK WHILE NAVIGATING IN 3D

(71) Applicant: COVIDIEN LP, Mansfield, MA (US)

(72) Inventors: Elad D. Lachmanovich, Modiin (IL); Benjamin Greenburg, Hod-Hasharon (IL); Eyal Klein, Herzliya (IL)

(73) Assignee: COVIDIEN LP, Mansfield, MA (US)

( * ) Notice: Subject to any disclaimer, the term of this patent is extended or adjusted under 35 U.S.C. 154(b) by 1146 days.

(21) Appl. No.: 14/790,107

(22) Filed: Jul. 2, 2015

(65) Prior Publication Data

US 2016/0000520 A1  Jan. 7, 2016

Related U.S. Application Data

(60) Provisional application No. 62/020,258, filed on Jul. 2, 2014.

(51) Int. Cl.
  *A61B 34/20* (2016.01)
  *A61B 6/03* (2006.01)
  (Continued)

(52) U.S. Cl.
  CPC .............. *A61B 6/032* (2013.01); *A61B 5/062* (2013.01); *A61B 34/20* (2016.02); *A61B 1/2676* (2013.01);
  (Continued)

(58) Field of Classification Search
  CPC . A61B 6/032; A61B 34/20; A61B 2034/2051; A61B 2034/105
  See application file for complete search history.

(56) References Cited

U.S. PATENT DOCUMENTS

| | | |
|---|---|---|
| 4,586,491 A | 5/1986 | Carpenter |
| 5,109,276 A | 4/1992 | Nudelman et al. |

(Continued)

FOREIGN PATENT DOCUMENTS

| | | |
|---|---|---|
| CN | 1658789 A | 8/2005 |
| DE | 102007015929 A1 | 10/2008 |

(Continued)

OTHER PUBLICATIONS

PCT International Search Report and Written Opinion for PCT/US2015/038787 dated Sep. 18, 2015.

(Continued)

*Primary Examiner* — Amanda Lauritzen Moher
*Assistant Examiner* — Brooke Lyn Klein
(74) *Attorney, Agent, or Firm* — Carter, DeLuca & Farrell LLP

(57) ABSTRACT

A system for navigating to a target, the system comprising an extended working channel having a lumen extending therethrough for receiving a tool, a computing device including a memory and at least one processor, a plurality of images stored in the memory, a program stored in the memory that, when executed by the at least one processor, presents a user interface. The user interface including, at least one image of the plurality of images depicting the target and a progression of the extended working channel through the airway, a probability treatment zone defining a probability distribution of a trajectory of the tool once deployed beyond an opening of the extended working channel displayed in the at least one image. The user interface is displayed on a display device.

10 Claims, 5 Drawing Sheets

(51) Int. Cl.
*A61B 5/06* (2006.01)
*A61B 34/10* (2016.01)
*A61B 10/04* (2006.01)
*A61B 1/267* (2006.01)
*A61B 17/00* (2006.01)

(52) U.S. Cl.
CPC ..... *A61B 10/04* (2013.01); *A61B 2017/00809* (2013.01); *A61B 2034/102* (2016.02); *A61B 2034/105* (2016.02); *A61B 2034/2051* (2016.02)

(56) References Cited

U.S. PATENT DOCUMENTS

| | | | |
|---|---|---|---|
| 5,301,061 | A | 4/1994 | Nakada et al. |
| 5,383,852 | A | 1/1995 | Stevens-Wright |
| 5,443,489 | A | 8/1995 | Ben-Haim |
| 5,645,065 | A | 7/1997 | Shapiro et al. |
| 5,730,129 | A | 3/1998 | Darrow et al. |
| 5,769,789 | A | 6/1998 | Wang et al. |
| 5,772,594 | A | 6/1998 | Barrick |
| 6,016,439 | A | 1/2000 | Acker |
| 6,035,229 | A | 3/2000 | Silverstein et al. |
| 6,061,588 | A | 5/2000 | Thornton et al. |
| 6,188,355 | B1 | 2/2001 | Gilboa |
| 6,246,784 | B1 | 6/2001 | Summers et al. |
| 6,345,112 | B1 | 2/2002 | Summers et al. |
| 6,443,894 | B1 | 9/2002 | Sumanaweera et al. |
| 6,468,265 | B1 | 10/2002 | Evans et al. |
| 6,676,659 | B2 | 1/2004 | Hutchins et al. |
| 6,796,963 | B2 | 9/2004 | Carpenter et al. |
| 7,233,820 | B2 * | 6/2007 | Gilboa ............... A61B 1/00154 600/407 |
| 2002/0137014 | A1 | 9/2002 | Anderson et al. |
| 2004/0152971 | A1 | 8/2004 | Kukuk |
| 2004/0249267 | A1 | 12/2004 | Gilboa |
| 2005/0182295 | A1 | 8/2005 | Soper et al. |
| 2008/0033417 | A1 | 2/2008 | Nields et al. |
| 2008/0234700 | A1 | 9/2008 | Trovato et al. |
| 2009/0156895 | A1 * | 6/2009 | Higgins ................ G06T 19/003 600/104 |
| 2009/0270712 | A1 * | 10/2009 | Raghavan .............. A61B 90/36 600/407 |
| 2010/0305439 | A1 | 12/2010 | Shai et al. |
| 2013/0315440 | A1 * | 11/2013 | Frank ................... G06K 9/3275 382/103 |
| 2014/0005706 | A1 | 1/2014 | Gelfand et al. |
| 2014/0187949 | A1 * | 7/2014 | Zhao ................... A61B 8/0841 600/443 |
| 2014/0259641 | A1 | 9/2014 | Brannan et al. |

FOREIGN PATENT DOCUMENTS

| | | |
|---|---|---|
| EP | 0600610 A2 | 6/1994 |
| EP | 0857461 A2 | 8/1998 |
| JP | 2007029232 A | 2/2007 |
| JP | 2008061858 A | 3/2008 |
| JP | 2008-136866 A | 6/2008 |
| JP | 2013022013 A | 2/2013 |
| JP | 2013-176559 A | 9/2013 |
| WO | 97/29682 A1 | 8/1997 |
| WO | 00/10456 A1 | 3/2000 |
| WO | 01/67035 A1 | 9/2001 |
| WO | 2006017489 A2 | 2/2006 |
| WO | 2011102012 A1 | 8/2011 |
| WO | 2013057620 A1 | 4/2013 |

OTHER PUBLICATIONS

The First Office Action issued in corresponding Chinese application No. 201580035783.X dated Feb. 2, 2018, with English translation, 22 pages.

Gibbs et al., "Three Dimensional Route Planning for Medical Image Reporting and Endoscopic Guidance," Aug. 1, 2008, The Pennsylvania State University, The Graduate School Department of Electrical Engineering, retrieved from http://media.proquest.com/media/pq/classic/doc/1633771611/fmt/ai/rep/NPDF?hl=&cit:auth=Gibbs, pp. 1-221.

Supplementary European Search Report dated Feb. 14, 2018 and issued in corresponding European Patent Application No. 15814744.

Notification of the Second Office Action dated Sep. 4, 2018 by the State Intellectual Property Office of the People's Republic of China in corresponding Chinese Patent Application No. 201580035783.X, with English translation.

Third Office Action issued in corresponding Chinese Appl. No. 201580035783.X dated Mar. 29, 2019, together with English language translation (15 pages).

Japanese Office Action issued in corresponding Appl. No. JP 2016-575426 dated Mar. 6, 2019, together with English language translation (7 pages).

Australian Examination Report issued in corresponding Appl. No. AU 2015284085 dated Mar. 14, 2019 (4 pages).

* cited by examiner

SYSTEM AND METHOD OF PROVIDING DISTANCE AND ORIENTATION FEEDBACK WHILE NAVIGATING IN 3D

CROSS REFERENCE TO RELATED APPLICATIONS

The present application claims the benefit of and priority to U.S. Provisional Patent Application Ser. No. 62/020,258 filed on Jul. 2, 2014, the entire contents of which are incorporated herein by reference.

BACKGROUND

1. Technical Field

The present disclosure relates to a system and method enabling navigation to a target outside of an airway, or to which access is otherwise limited and to systems and methods for assessing the ability of tools to reach the target.

2. Description of Related Art

A common device for inspecting and navigating the airway of a patient is a bronchoscope. Typically, the bronchoscope is inserted into a patient's airways through the patient's nose or mouth and can extend into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools, therapeutic instruments can be inserted.

In navigating to a target, bronchoscopes, however, are limited in how far they may be advanced through the airways due to their size. Where the bronchoscope is too large to reach a target location deep in the lungs a clinician may utilize certain real-time imaging modalities such as fluoroscopy. Fluoroscopic images, while useful present certain drawbacks for navigation as it is often difficult to distinguish luminal passageways from solid tissue. Moreover, the images generated by the fluoroscope are two-dimensional whereas navigating the airways of a patient requires the ability to maneuver in three dimensions.

To address these aforementioned issues, systems have been developed that enable the development of three-dimensional models of the airways or other luminal networks, typically from a series of computed tomography (CT) images. One such system has been developed as part of the ILOGIC® ELECTROMAGNETIC NAVIGATION BRONCHOSCOPY® (ENB™), system currently sold by Covidien LP. The details of such a system are described in the commonly assigned U.S. Pat. No. 7,233,820 filed on Mar. 29, 2004 to Gilboa and entitled ENDOSCOPE STRUCTURES AND TECHNIQUES FOR NAVIGATING TO A TARGET IN BRANCHED STRUCTURE, the contents of which are incorporated herein by reference.

While the system as described in U.S. Pat. No. 7,233,820 is quite capable, there is always a need for development of improvements and additions to such systems.

In addition, during the performance of an ELECTROMAGNETIC NAVIGATION BRONCHOSCOPY® ("ENB") procedure using an electromagnetic navigation ("EMN") system, a clinician may be required to navigate to a target outside of an airway (or to a target which access is otherwise limited) and during this navigation the catheter may have to be parked short of the target. This is done in preparation for insertion of an access tool or needle which may have to penetrate the airway wall in order to reach the target. It is very common for a user to prefer moving as close as possible to the target. However, this sometimes overlooks the factor of catheter orientation in relation to the target, which is of equal or greater importance to reaching the target, compared to the distance from the target. Furthermore, when an access tool, needle or biopsy tool is deployed out of the catheter, it may deflect due to tissue physiology or geometry, catheter bending or other reasons.

To address this issue, the present disclosure is directed to systems and methods of assessing the ability of a tool to reach and interact with the target located outside of an airway, or to which access is otherwise limited, from a location inside of the airway and identifying optimal locations from which to achieve such access and interaction.

SUMMARY

Provided in accordance with the present disclosure are a system and method for navigating to a target outside of an airway, or to which access is otherwise limited.

An aspect of the present disclosure relates to a system for navigating to a target, the system comprising: an extended working channel defining a lumen extending therethrough for receiving a tool; a computing device including a memory and at least one processor; a plurality of images stored in the memory; a display device that displays a user interface; and a program stored in the memory that, when executed by the at least one processor, presents the user interface, the user interface including: at least one image of the plurality of images depicting the target and a progression of the extended working channel through the airway; and a probability treatment zone defining a probability distribution of a trajectory of the tool once deployed beyond an opening of the extended working channel displayed in the at least one image.

In another aspect of the present disclosure, the user interface is configured to depict movement of the extended working channel allowing the user to position the probability treatment zone in an orientation so that at least a portion of the target is encompassed by the probability treatment zone.

In another aspect of the present disclosure, the user interface is further configured to allow the user to display the probability treatment zone as a three-dimensional volumetric shape.

In another aspect of the present disclosure, the user interface is configured such that an increase in a target volume inside the probability treatment zone indicates an increase in probability that the tool will interact with a portion of the target inside the probability treatment zone.

In another aspect of the present disclosure, the user interface is configured such that a length of the probability treatment zone from the opening of the extended working channel corresponds to a maximum effective range the tool can be deployed beyond the opening of the extended working channel.

In another aspect of the present disclosure, the user interface is further configured to allow the user to display the probability treatment zone as a two-dimensional shape.

In another aspect of the present disclosure, the user interface is further configured to display the probability treatment zone with a first indicator, wherein the first indicator includes a status of an orientation of the tool with respect to the target and a second indicator, where the second indicator includes a status of a range of the tool with respect to the target.

In another aspect of the present disclosure, when the portion of the target is encompassed by the probability treatment zone, the status of the first indicator changes indicate that the orientation of the tool allows the tool to interact with the target.

In another aspect of the present disclosure, when the range from the opening of the extended working channel to the target is less than a maximum deployable range of the tool, the status of the second indicator changes to indicate that the range of the tool allows the tool to interact with the target.

In another aspect of the present disclosure, the tool is selected from the group consisting of needle, an access tool, a biopsy tool, a therapeutic material application tool, and an ablation tool.

In another aspect of the present disclosure, the probability treatment zone is adjusted based on the tool selected.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, wherein.

DETAILED DESCRIPTION

The present disclosure is directed to a system and method of determining and displaying proximity to a target, and presenting a graphical display of an area a biopsy tool, or other surgical tool, might traverse if extended from an Extended Working Channel in the direction of the target. With such a system a clinician can determine whether a change of position is desirable or necessary prior to extracting a biopsy or treating the targeted tissue and have increased confidence that a biopsy taken or a treatment undertaken has been of the target and not tissue merely in the proximity of the target.

An EMN procedure generally involves at least two phases: (1) planning a pathway to a target located within, or adjacent to, the patient's airways; and (2) navigating a probe to the target along the planned pathway. These phases are generally referred to as (1) "planning" and (2) "navigation."

The planning phase of an EMN procedure is more fully described in commonly-owned U.S. patent application Ser. Nos. 13/838,805; 13/838,997; and 13/839,224, all entitled "Pathway Planning System and Method," filed on Mar. 15, 2013, by Baker, the entire contents of which are hereby incorporated by reference.

Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be used during the planning phase of the ENB procedure.

Figure 1:
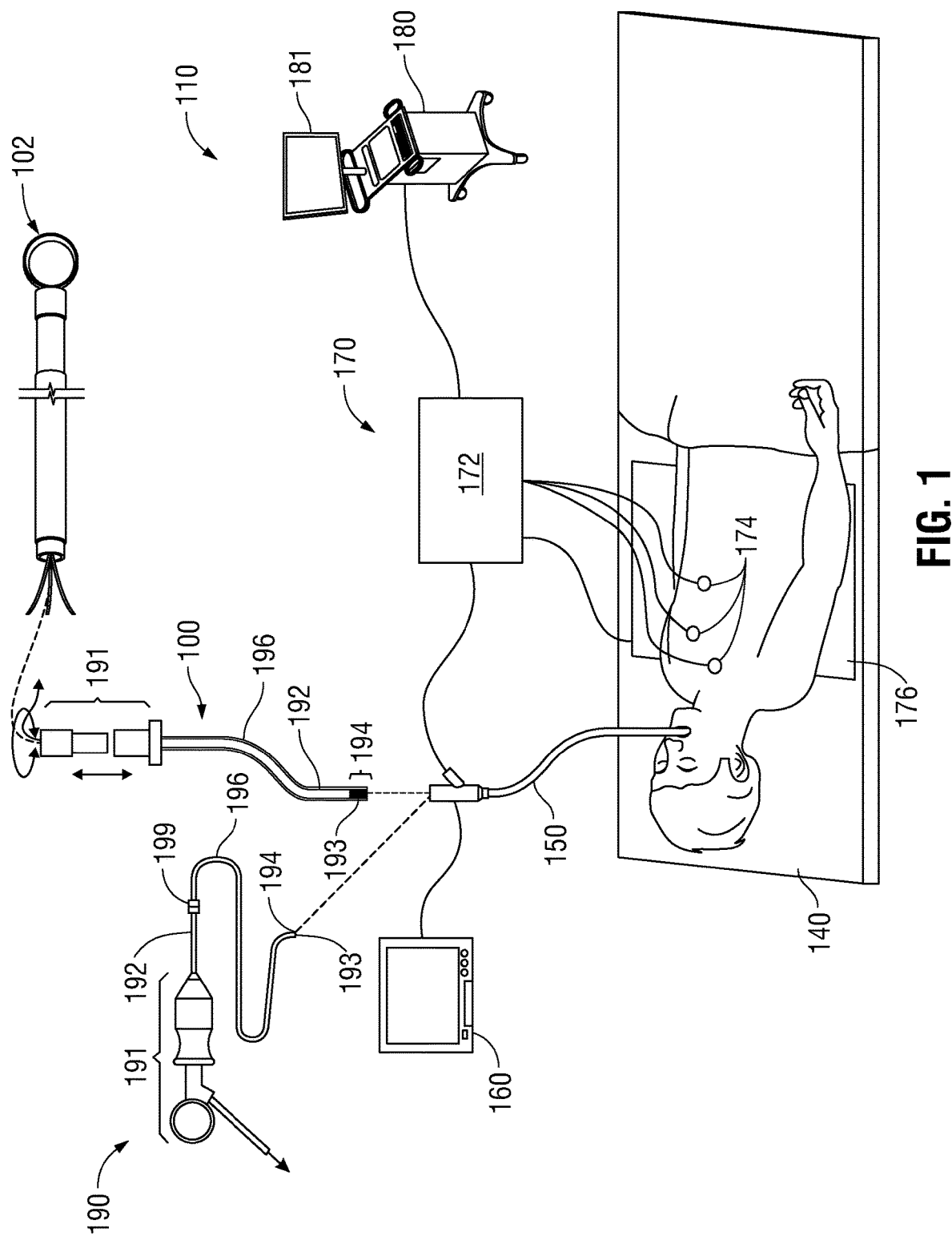
FIG. 1 is a perspective view of an electromagnetic navigation system in accordance with the present disclosure.

With reference to FIG. 1, an EMN system 110 is provided in accordance with the present disclosure. One such ENM system is the ENB system currently sold by Covidien LP. Among other tasks that may be performed using EMN system 110 are planning a pathway to target tissue, navigating a positioning assembly to the target tissue, navigating a biopsy tool to the target tissue to obtain a tissue sample from the target tissue using the biopsy tool, and digitally marking the location where the tissue sample was obtained, and placing one or more echogenic markers at or around the target.

EMN system 110 generally includes an operating table 140 configured to support a patient; a bronchoscope 150 configured for insertion through the patient's mouth and/or nose into the patient's airways; monitoring equipment 160 coupled to bronchoscope 150 for displaying video images received from bronchoscope 150; a tracking system 170 including a tracking module 172, a plurality of reference sensors 174, an electromagnetic field generator 176; and a workstation 180 including software and/or hardware used to facilitate pathway planning, identification of target tissue, navigation to target tissue, and digitally marking the biopsy location.

FIG. 1 also depicts two types of catheter guide assemblies 100, 190. Both catheter guide assemblies 100, 190 are usable with EMN system 110 and share a number of common components. Each catheter guide assembly 100, 190 include a handle 191, which is connected to an extended working channel (EWC) 196. The EWC 196 is sized for placement into the working channel of a bronchoscope 150. In operation, a locatable guide 192, including an electromagnetic (EM) sensor 194, is inserted into EWC 196 and locked into position such that the sensor 194 extends a desired distance beyond the distal tip 193 of EWC 196. The location of the EM sensor 194, and therefore the distal end of EWC 196, within an electromagnetic field generated by the electromagnetic field generator 176, can be derived by the tracking module 172, and the workstation 180. Catheter guide assemblies 100, 190 have different operating mechanisms, but the handle 191 can be manipulated by rotation and compression to steer the distal tip 193 of locatable guide 192 inserted into EWC 196. Catheter guide assembly 190 is currently marketed and sold by Covidien LP under the name SUPERDIMENSION® Procedure Kits, similarly catheter guide assembly 100 is currently sold by Covidien LP under the name EDGE™ Procedure Kits, both kits include the 191, extended working channel 196, and locatable guide 192. For a more detailed description of the catheter guide assemblies 100, 190, reference is made to commonly-owned U.S. patent application Ser. No. 13/836,203 filed on Mar. 15, 2013 by Ladtkow et al., the entire contents of which are hereby incorporated by reference.

As illustrated in FIG. 1, the patient is shown lying on operating table 140 with bronchoscope 150 inserted through the patient's mouth and into the patient's airways. Bronchoscope 150 includes a source of illumination and a video imaging system (not explicitly shown) and is coupled to monitoring equipment 160, e.g., a video display, for displaying the video images received from the video imaging system of bronchoscope 150.

Catheter guide assemblies 100, 190 including locatable guide 192 and EWC 196 are configured for insertion through a working channel of bronchoscope 50 into the patient's airways (although the catheter guide assemblies 100, 190 may alternatively be used without bronchoscope 50). The locatable guide 192 and EWC 196 are selectively lockable relative to one another via a locking mechanism 199. A six degrees-of-freedom electromagnetic tracking system 170 (e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system), is utilized for performing navigation, although other configurations are also contemplated. Tracking system 170 is configured for use with catheter guide assemblies 100, 190 to track the position of the EM sensor 194 as it moves in conjunction with EWC 196 through the airways of the patient, as detailed below.

As further shown in FIG. 1, electromagnetic field generator 176 is positioned beneath the patient. Electromagnetic field generator 176 and the plurality of reference sensors 174 are interconnected with tracking module 172, which derives the location of each reference sensor 174 in six degrees of freedom. One or more of reference sensors 174 are attached to the chest of the patient. The six degrees of freedom coordinates of reference sensors 174 are sent to workstation 180, which includes application 181 where data from sensors 174 is used to calculate a patient coordinate frame of reference.

Further shown in FIG. 1 is a catheter biopsy tool 102 that is insertable into catheter guide assemblies 100, 190 following navigation to a target and removal of locatable guide 192. Biopsy tool 102 is used to collect one or more tissue sample from the target tissue. As detailed below, biopsy tool 102 is further configured for use in conjunction with tracking system 170 to facilitate navigation of biopsy tool 102 to the target tissue, tracking of a location of biopsy tool 102 as it is manipulated relative to the target tissue to obtain the tissue sample, and/or marking the location where the tissue sample was obtained.

Although navigation is detailed above with respect to EM sensor 194 being included in locatable guide 192 it is also envisioned that EM sensor 194 may be embedded or incorporated within biopsy tool 102 where biopsy tool 102 may alternatively be utilized for navigation without need of locatable guide 192 or the necessary tool exchanges that use of locatable guide 192 requires. A variety of useable biopsy tools are described in U.S. Provisional Patent Application Nos. 61/906,732 and 61/906,762 both entitled DEVICES, SYSTEMS, AND METHODS FOR NAVIGATING A BIOPSY TOOL TO A TARGET LOCATION AND OBTAINING A TISSUE SAMPLE USING THE SAME, filed Nov. 20, 2013 and U.S.

Provisional Patent Application No. 61/955,407 having the same title and filed Mar. 14, 2014, the entire contents of each of which are incorporated herein by reference and useable with EMN system 110 as described herein.

During procedure planning, workstation 180 utilizes CT image data, or other image data in DICOM format, for generating and viewing a three-dimensional model ("3D model") of the patient's airways. The 3D model and image data derived from the 3D model enables the identification of target tissue (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor 181 associated with workstation 180, or in any other suitable fashion. Using workstation 180, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure.

During navigation, EM sensor 194, in conjunction with tracking system 170, enables tracking of EM sensor 94 and/or biopsy tool 102 as EM sensor 194 or biopsy tool 102 is advanced through the patient's airways.

Figure 2:
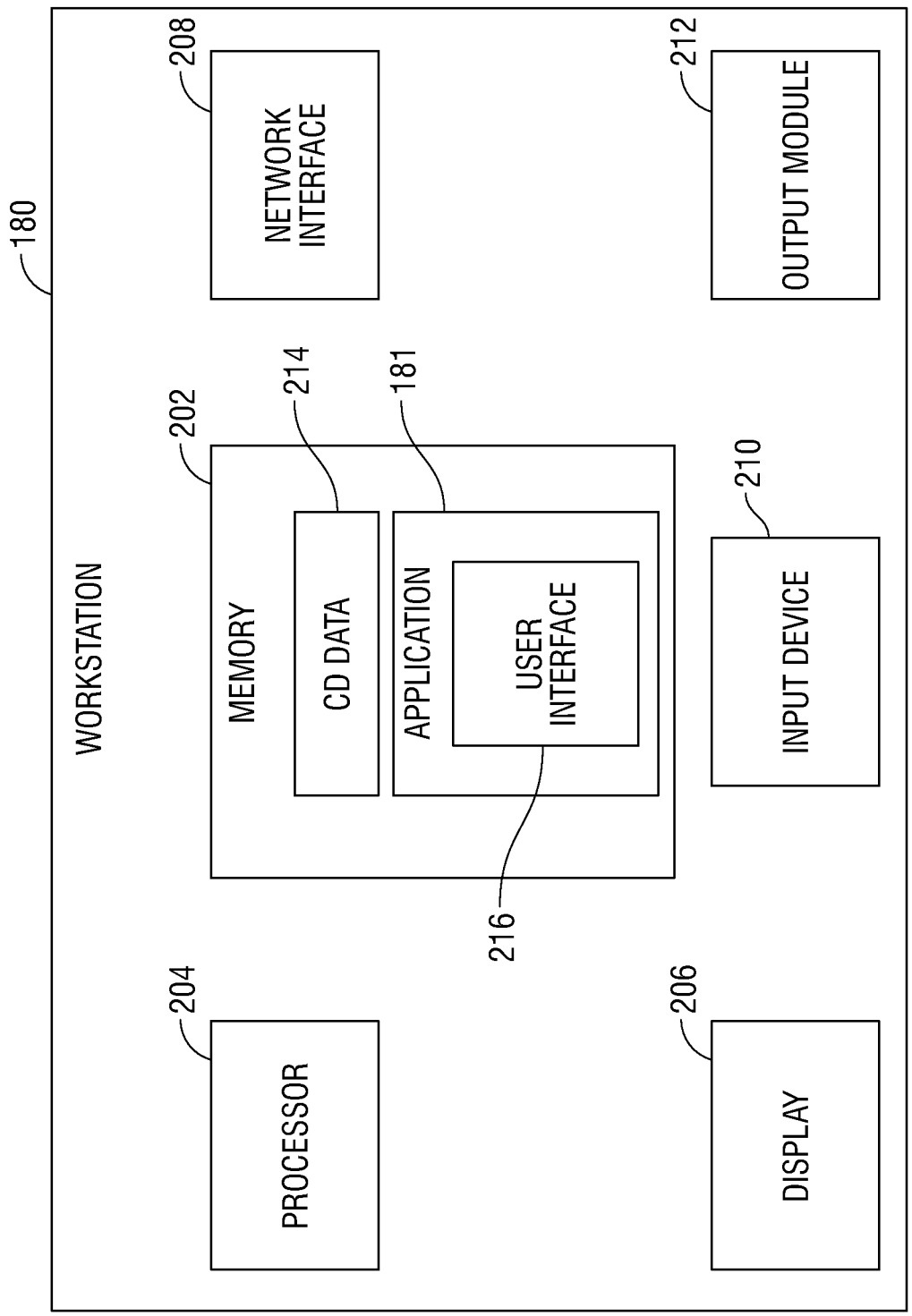
FIG. 2 is a schematic diagram of a workstation configured for use with the system of FIG. 1.

Turning now to FIG. 2, there is shown a system diagram of workstation 180. Workstation 180 may include memory 202, which further includes CT data 214 and application 181 including user interface 216, processor 204, display 206, network interface 208, input device 210, and/or output module 212.

Figure 3:
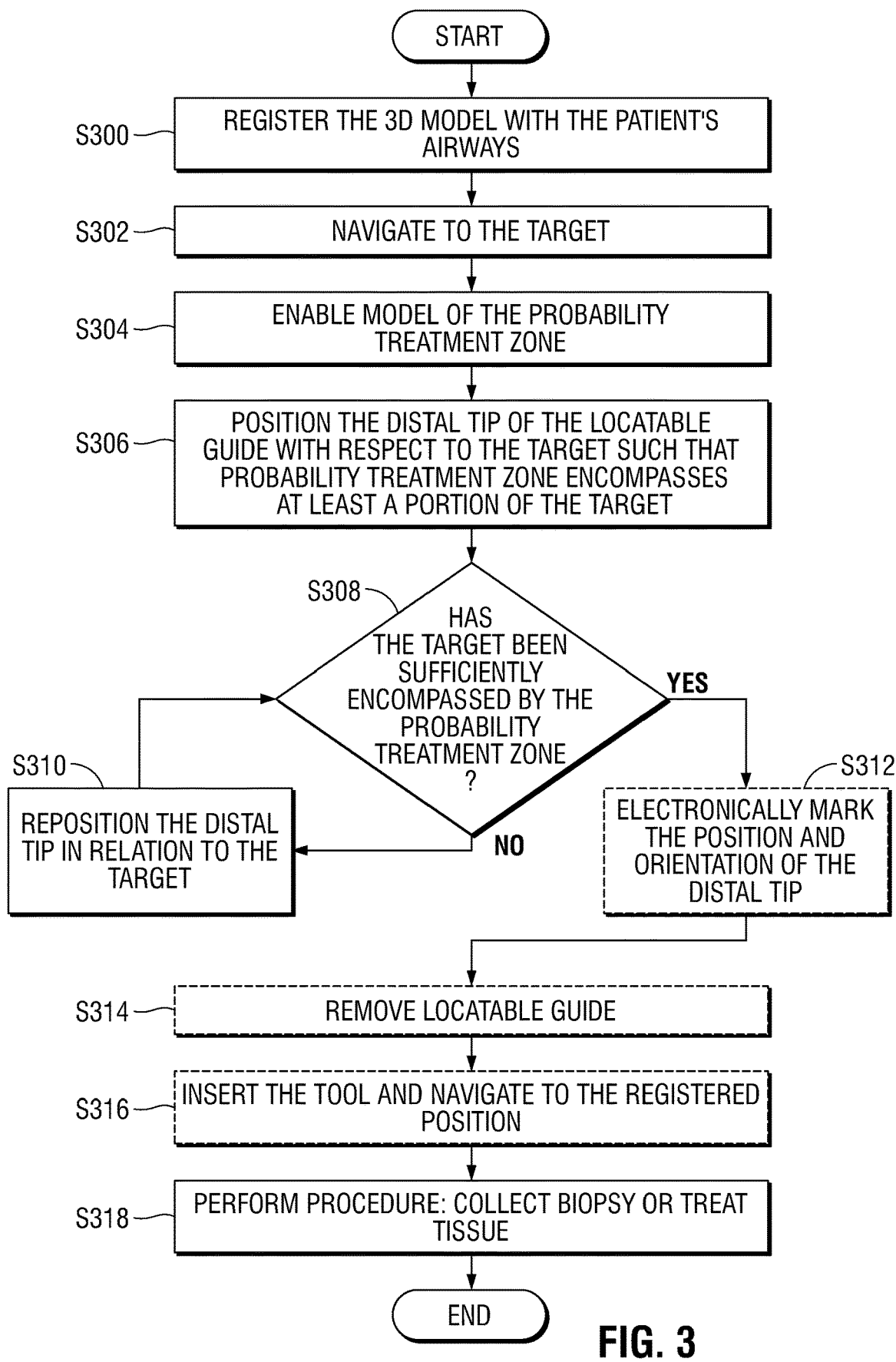
FIG. 3 is a flowchart illustrating a method for navigating to the location of a target outside of an airway, or to which access is otherwise limited, provided in accordance with the present disclosure.

Referring now to FIG. 3, there is shown a flowchart of an example method for navigating to a target outside of an airway, or to which access is otherwise limited, during a procedure in accordance with the present disclosure. Prior to the start of navigation, the clinician loads a navigation plan including the 3D model of the lungs of the patient and the planned pathways to identified targets into a navigation application 181 from memory 202, via network interface 208, or a USB drive. An example of the navigation application can be found in commonly assigned U.S. Provisional Patent Application No. 62/020,240 filed Jul. 2, 2014 and entitled SYSTEM AND METHOD FOR NAVIGATING WITHIN THE LUNG, the entire contents of which are incorporated herein by reference.

To perform automatic registration, the clinician advances bronchoscope 150, locatable guide 192, and EWC 196 into each region of the patient's airways in step S300 until registration has occurred between the location of EM sensor 194 of locatable guide 192 and the 3D model and other data in the navigation plan. Details of this registration are set forth in Provisional Application 62/020,220 filed on Jul. 2, 2014 the contents of which are incorporated herein by reference. Alternative registration techniques including manual are possible and described in detail in U.S. Pat. No. 7,233,820 entitled "ENDOSCOPE STRUCTURES AND TECHNIQUES FOR NAVIGATING TO A TARGET IN BRANCHED STRUCTURE" the entire contents of which are incorporated herein by reference.

Figure 5:
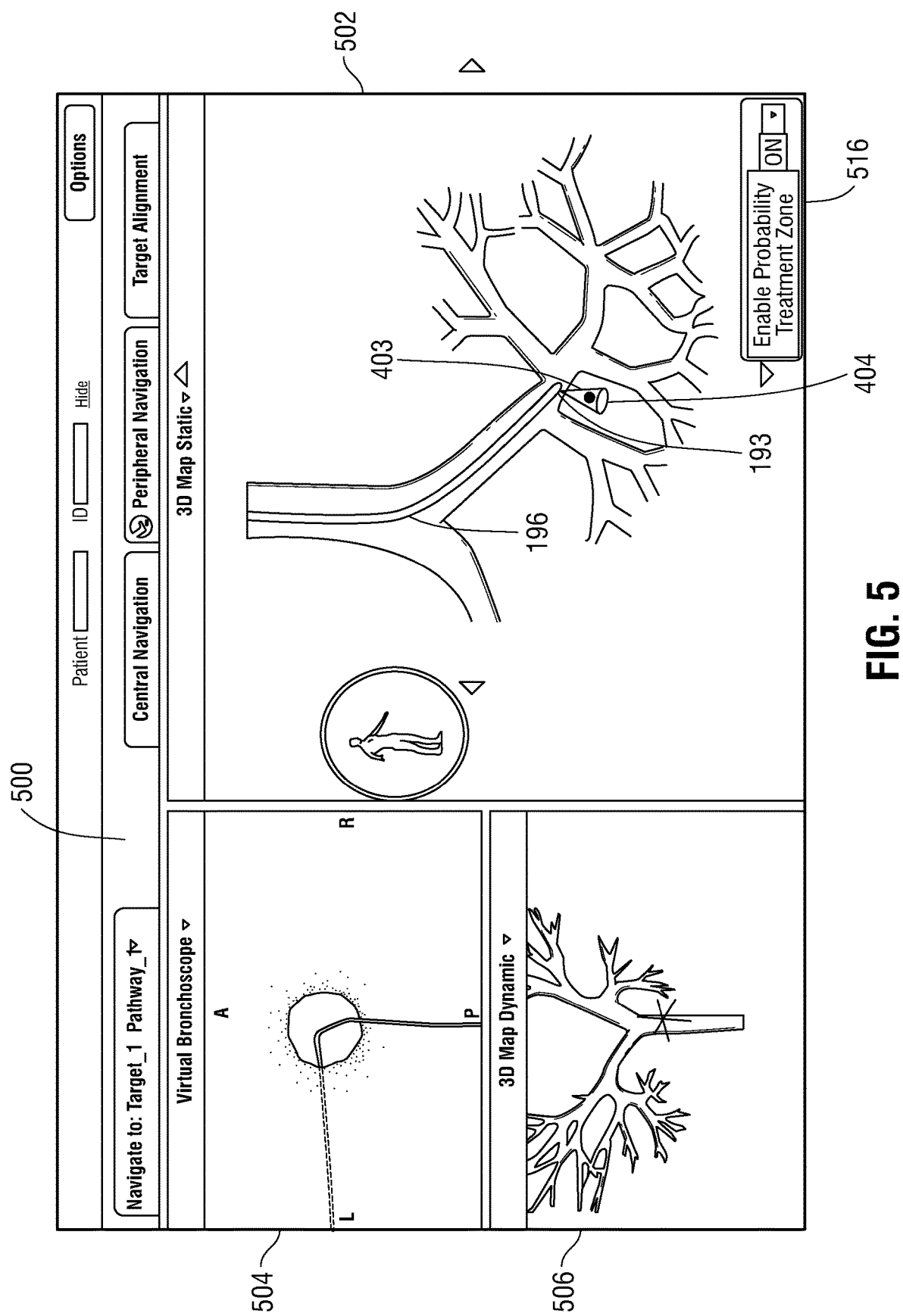
FIG. 5. is an illustration of a user interface of the workstation of FIG. 1 and FIG. 2 presenting multiple views of 3D models for navigating to a target location in accordance with the present disclosure.

Once registered, the clinician continues to navigate to a target following a pathway identified in the pathway plan at step S302. As EWC 196 and locatable guide 192 approach the target, the clinician either manually enables or the application automatically enables a display of the model of the probability treatment zone ("PTZ") 404 at step S304. Once enabled, the clinician navigates EWC 196 with respect to the target 403, as shown in FIG. 5. As the clinician, following the pathway plan, approaches the target 403, EWC 196 can be positioned such that the display of PTZ 404 interacts with the display target 403. Specifically, the clinician navigates EWC 196 such that PTZ 404 encompasses a sufficient portion of the target 403 that the clinician can have reasonable certainty that biopsy or treatment deployed will properly impact the target 403 and not surrounding tissue, at steps S306, S308, and S310. The clinician has the ability to reposition the EWC 196, at step S310, to further ensure that an increased amount of PTZ 404 encompasses target 403. The clinician, through the repositioning of the EWC 196 in relation to the target 404, thus repositions PTZ 404. Once satisfied with the position of PTZ 404 with respect to target 403, the clinician may optionally mark the position and orientation of the EWC 196, at step S312. The locatable guide 192 (if used) may be removed at step S314, and a biopsy or treatment tool inserted through EWC 196 at step 316, to perform the necessary biopsy or treatment at step S318.

Figure 4A:
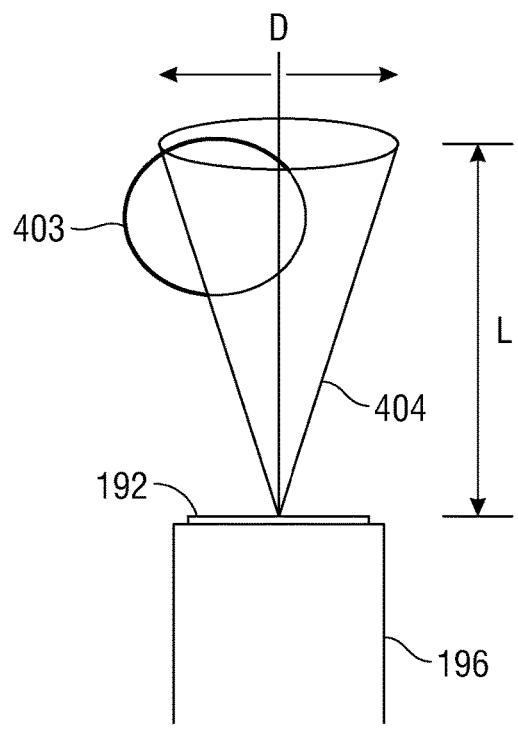
FIG. 4A is an illustration of a probability treatment zone displayed as a three-dimensional shape.

Referring now to FIG. 4A, PTZ 404 is depicted as a three-dimensional volumetric shape. In this instance by a cone shaped projection emanating from the center point of distal tip 193 of EWC 196 or locatable guide 192. The cone length L indicates the maximum useful or effective distance a laparoscopic tool (e.g., a biopsy tool, a microwave or radiation ablation tool, a chemotherapy tool, a therapeutic medication application tool, a brachytherapy tool, a marker placement tool, or other similar laparoscopic tools) can extend beyond the distal end of EWC 196. The cone diameter D indicates the maximum probable distribution or deflection of a tool when extended beyond EWC 196. As will be appreciated by those of skill in the art, the maximum length for which the tool is useful or effective may vary depending on the tool employed, and a selection feature may be enabled on the user interface of the navigation application to vary the length of the cone. Although shown as a conical overlay deploying beyond EWC 192 opening, PTZ 404 may be configured to have various shapes depending on physical attributes of the tool being employed.

Figure 4B:
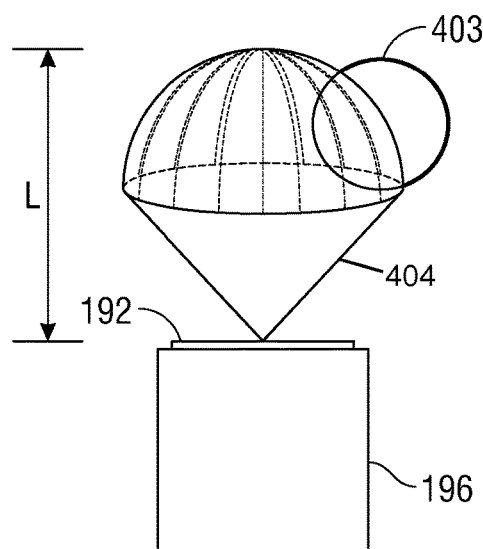
FIG. 4B is another embodiment of an illustration of a probability treatment zone displayed as another three-dimensional shape.

In FIG. 4B, PTZ 404 is depicted as a three-dimensional volumetric cone shaped projection with a spherical cap emanating from the center point of distal tip 193 of EWC 196 or locatable guide 192. The depiction in FIG. 4B details the use of a therapeutic medication application tool. The cone shaped projection with a spherical cap (or other applicable shape) indicates the maximum probable distribution of a therapeutic medication which is distributed beyond the distal end of EWC 196. In one such embodiment, the therapeutic medication exits the distal tip 193 of EWC 196 or locatable guide 192 in a three-dimensional volumetric small cone shape followed by forming a volumetric spherical shape as the therapeutic medication continues to be dispersed. Although the therapeutic medication may continue to be distributed beyond the volumetric shape shown in FIG. 4B the volumetric shape details the maximum volume for which the therapeutic medication is useful or effective.

Figure 4C:
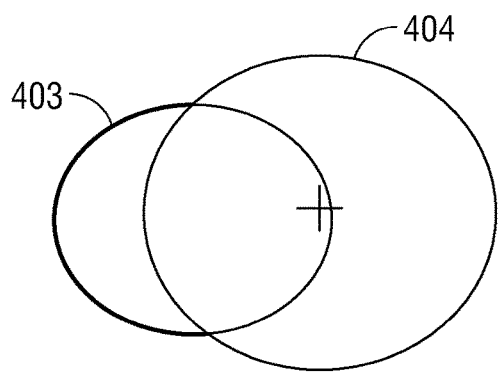
FIG. 4C depicts two illustration of a probability treatment zone displayed as a two-dimensional shape.
Figure 4C:
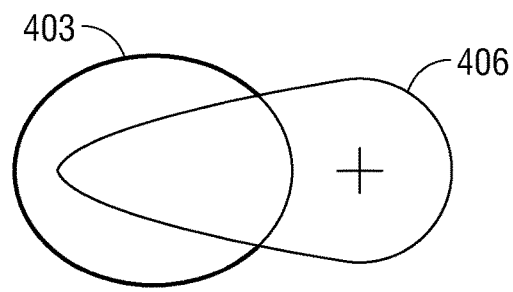

FIG. 4C shows a comparison of two projections viewed from EWC 196, a cone 404 similar to that in FIG. 4A and an unbalanced ellipsoid 406. As will be appreciated by those of skill in the art the unbalanced ellipsoid may represent the deflection of a tool which flexes in one direction more than in others.

In a further embodiment, PTZ 404 may have different colors, and may change color as more of the target 403 is within PTZ 404. Thus, the clinician is provided feedback regarding the sufficiency of the coverage of target 403, within PTZ 404, and can have greater confidence of reaching the target 403 as PTZ 404 changes from a red color indicating too little or no target 403 in PTZ 404, to green indicating that greater than some threshold portion of the target 403 is within PTZ 404.

In addition, PTZ 404 may contain various indicators which enable the clinician to determine both the distance to target 403 and the orientation of distal tip 193 of EWC 196 with respect to target 403. Indicators may include visual, tactile, or audio changes to indicate to the clinician that distal tip 193 of EWC 196 is in a position and orientation which allows the tool to interact with the target 403. For example, as PTZ 404 is manipulated to a view as shown in FIG. 4C, statuses of indicators may change to ensure that the distance L (shown in FIG. 4A) is better understood. Once the distance L is greater than the distance from distal tip 193 of EWC 196 to target 403, the status of the indicators changes to notify the clinician that that target 403 is within PTZ 404.

In accordance with embodiments of the present disclosure, once registration is complete, display 181 presents user interface 500 to the clinician with a number of views 502, 504, and 506, as shown in FIG. 5 to assist the clinician in navigating locatable guide 192 and EWC 196 to the target 403. User interface 500 may include a local view (3D map static) 502, a virtual bronchoscope view 504, and a 3D map dynamic view 506. Local view 502 also presents the clinician with a visualization of the distal tip 193 and EM sensor 194 of locatable guide 192. Other views may be presented without departing from the scope of the present disclosure. As EWC 196 and locatable guide 192 advance, each of the views 502, 504, and 506 is updated to account for the change in location.

As shown in FIG. 5, PTZ 404 may be a graphic overlay applied by the navigation application when EWC 196 is in proximity of the target 403, the target 403 having been identified by the clinician during the pathway planning phase of the procedure, described above. The PTZ 404 may be presented in any of the views depicted on user interface 500 to assist in the final orientation of EWC 196. As noted above, the user interface 500 may include a user active Enable Probability Treatment Zone View button 516 allowing the clinician to display the 404 PTZ in any view depicted on the user interface 500. In some embodiments this may be particularly useful in 3D viewing modes such the 3D map and/or virtual bronchoscopy view 504.

Referring back to the computer-readable media of FIG. 2, memory 202 includes any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 180.

Further aspects of the system and method are described in co-pending and commonly-owned U.S. Provisional Patent Application Ser. No. 62/020,220 entitled "Real-Time Automatic Registration Feedback," filed on Jul. 2, 2014, by Brown et al.; U.S. Provisional Patent Application Ser. No. 62/020,177 entitled "Methods for Marking Biopsy Location," filed on Jul. 2, 2014, by Brown; U.S. Provisional Patent Application Ser. No. 62/020,240 entitled "System and Method for Navigating Within the Lung," filed on Jul. 2, 2014, by Brown et al.; U.S. Provisional Patent Application Ser. No. 62/020,238 entitled "Intelligent Display," filed on Jul. 2, 2014, by Kehat et al.; U.S. Provisional Patent Application Ser. No. 62/020,242 entitled "Unified Coordinate System for Multiple CT Scans of Patient Lungs," filed on Jul. 2, 2014, by Greenburg; U.S. Provisional Patent Application Ser. No. 62/020,245 entitled "Alignment CT," filed on Jul. 2, 2014, by Klein et al.; U.S. Provisional Patent Application Ser. No. 62/020,250 entitled "Algorithm for Fluoroscopic Pose Estimation," filed on Jul. 2, 2014, by Merlet; U.S. Provisional Patent Application Ser. No. 62/020,261 entitled "System and Method for Segmentation of Lung," filed on Jul. 2, 2014, by Markov et al.; U.S. Provisional Patent Application Ser. No. 62/020,253 entitled "Trachea Marking," filed on Jul. 2, 2014, by Lachmanovich et al.; and U.S. Provisional Patent Application Ser. No. 62/020,262 entitled "Dynamic 3D Lung Map View for Tool Navigation Inside the Lung," filed on Jul. 2, 2014, by Weingarten et al., the entire contents of all of which are hereby incorporated by reference.

Detailed embodiments of devices, systems incorporating such devices, and methods using the same have been described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure. While the preceding embodiments were described in terms of bronchoscopy of a patient's airways, those skilled in the art will realize that the same or similar devices, systems, and methods may be used in other lumen networks, such as, for example, the vascular, lymphatic, and/or gastrointestinal networks as well.

What is claimed is:

1. A system for navigating to a target, the system comprising:
   a bronchoscope;
   a catheter configured to be advanced through a working channel of the bronchoscope and defining a lumen extending therethrough for receiving a therapeutic medication application tool;
   a computing device including a memory and at least one processor;
   a plurality of images stored in the memory;
   a display device that displays a user interface; and
   a program stored in the memory that, when executed by the at least one processor, causes the computing device to:
   display, via the user interface of the display device, at least one image of the plurality of images depicting a target and a progression of the catheter through an airway;
   determine a probability treatment zone including a maximum probable distribution of a therapeutic medication distributed by the therapeutic medication application tool once deployed on a trajectory beyond a distal end of the catheter,
   wherein:
   the probability treatment zone is determined based on a maximum distance the therapeutic medication application tool can extend through and beyond the distal end of the catheter; and
   the maximum probable distribution is graphically represented via the user interface by a volumetric shape overlaid on the at least one image of the plurality of images depicting the target, the volumetric shape corresponding to the probability treatment zone and including:
   a cone tapering from a flat base spaced distally from the distal end of the catheter to an apex disposed at the distal end of the catheter; and
   a hemisphere having a flat base coplanar with the flat base of the cone and a curved surface extending distally from the flat base of the hemisphere;
   display, via the user interface of the display device, the maximum probable distribution of the therapeutic medication in the at least one image of the plurality of images; and
   display, via the user interface of the display device, the target at least partially encompassed by the volumetric shape to depict an overlap area between the target and the volumetric shape, wherein the volumetric shape is displayed in a first color in response to at least a threshold portion of the target being encompassed by the volumetric shape and in a second color in response to less than the threshold portion of the target being encompassed by the volumetric shape.

2. The system according to claim 1, wherein the user interface is configured to depict movement of the catheter and corresponding movement of the volumetric shape, thereby allowing a user to move the catheter relative to the target to effect corresponding movement of the volumetric shape relative to the at least one image of the plurality of images depicting the target on the user interface.

3. The system according to claim 1, wherein the user interface is configured such that an increase in the overlap area between the target and the probability treatment zone indicates an increase in probability that the therapeutic medication application tool will interact with the target.

4. The system according to claim 1, wherein the user interface is further configured to display the probability treatment zone as a two-dimensional shape.

5. The system according to claim 1, wherein the user interface is further configured to display the probability treatment zone with a first indicator including a status of an orientation of the catheter with respect to the target and a second indicator including a status of a range of the therapeutic medication application tool with respect to the target.

6. The system according to claim 2, wherein the user interface is further configured to display the volumetric shape as a three-dimensional volumetric shape.

7. The system according to claim 5, wherein the status of the first indicator changes based on the target being at least partially encompassed by the volumetric shape.

8. The system according to claim 5, wherein when the range from the opening of the catheter to the target is less than a maximum deployable range of the therapeutic medication application tool, the status of the second indicator changes to indicate that the range of the therapeutic medication application tool allows the therapeutic medication application tool to interact with the target.

9. A system for navigating to a target, the system comprising:
   a bronchoscope;
   a catheter configured to be advanced through the bronchoscope and defining a lumen extending therethrough for receiving a therapeutic medication application tool and for guiding the therapeutic medication application tool to a target in a patient;
   a computing device including a memory and at least one processor;
   a display device in communication with the computing device; and
   a program stored in the memory that, when executed by the at least one processor, causes the computing device to:
      determine a maximum probable distribution of a therapeutic medication distributed by the therapeutic medication application tool, wherein the maximum probable distribution is graphically represented via the display device by a volumetric shape overlaid on an image depicting the target, the volumetric shape including:
         a cone extending distally from an apex disposed at the distal end of the catheter to a flat base spaced distally from the distal end of the catheter; and
         a hemisphere having a flat base coplanar with the flat base of the cone;
      display, via the display device, the maximum probable distribution of the therapeutic medication; and
      display, via the display device, the target at least partially encompassed by the volumetric shape to depict an overlap area between the target and the volumetric shape, wherein the volumetric shape is displayed in a first color in response to at least a threshold portion of the target being encompassed by the volumetric shape and in a second color in response to less than the threshold portion of the target being encompassed by the volumetric shape.

10. The system according to claim 9, wherein the display device is configured to depict movement of the catheter and corresponding movement of the volumetric shape, thereby allowing a user to move the catheter relative to the target to effect corresponding movement of the volumetric shape relative to the image depicting the target displayed on the display device.

* * * * *